(12) United States Patent
Haimerl

(10) Patent No.: US 7,753,848 B2
(45) Date of Patent: Jul. 13, 2010

(54) DETERMINING SPEED-OF-SOUND FACTORS IN ULTRASOUND IMAGES OF A BODY

(75) Inventor: Martin Haimerl, Gilching (DE)

(73) Assignee: BrainLAB AG, Feldkirchen (DE)

( * ) Notice: Subject to any disclaimer, the term of this patent is extended or adjusted under 35 U.S.C. 154(b) by 841 days.

(21) Appl. No.: 11/559,150

(22) Filed: Nov. 13, 2006

(65) Prior Publication Data

US 2007/0167757 A1    Jul. 19, 2007

Related U.S. Application Data

(60) Provisional application No. 60/738,548, filed on Nov. 21, 2005.

(30) Foreign Application Priority Data

Nov. 11, 2005    (EP) .................................. 05024671

(51) Int. Cl.
*A61B 8/00* (2006.01)
*G01H 5/00* (2006.01)
(52) U.S. Cl. .......................... 600/443; 600/438; 73/597
(58) Field of Classification Search ................ 600/437, 600/438, 443; 382/128, 276, 286, 294; 73/597
See application file for complete search history.

(56) References Cited

U.S. PATENT DOCUMENTS

| 7,379,769 B2 * | 5/2008 | Piron et al. ................. 600/415 |
| 2005/0080333 A1 | 4/2005 | Piron et al. |

OTHER PUBLICATIONS

Krucker et al., "Sound Speed Estimation using Automatic Ultrasound Image Registration", IEEE transactions on Ultrasonics, Ferroelectrics, and Frequency Control, vol. 51, No. 9, Sep. 2004, pp. 1095-1106.*
Duncan et al., "Self-calibrating Ultrasound-to-CT Bone Registration", MICCAI Oct. 2005, LNCS 3749, pp. 605-612.
Fookes, C. et al., Institute of Electrical and Electronics Engineers, "The Use of Mutual Information for Rigid Medical Image Registration: A Review", IEEE, Oct. 2002, pp. 689-694.
Krücker, J.F. et al., "Sound Speed Estimation Using Ultrasound Image Registration", Biomedical Imaging, 2002 Proceedings. IEEE, Jul. 2002, pp. 437-440.
Krücker, J.F. et al, "Registration-Based Sound Speed Estimation in Phantoms With Acoustically Vaporized Droplets", 2002 IEEE, pp. 1729-1732.

(Continued)

*Primary Examiner*—Eric F Winakur
*Assistant Examiner*—Katherine L Fernandez
(74) *Attorney, Agent, or Firm*—Renner, Otto, Boisselle & Sklar, LLP

(57) ABSTRACT

A method for determining speed-of-sound factors in ultrasound images of a body, includes: capturing at least two ultrasound images of an internal body region from different directions; registering the at least two ultrasound images with respect to a corresponding region in a body reference model; comparing two-dimensional registrations of each of the at least two ultrasound images with a registration of at least one other ultrasound image captured from a different direction, or with another reference registration; and determining the speed-of-sound factor for each individual ultrasound direction from the comparison of reference model point distances for a particular registered structure.

17 Claims, 3 Drawing Sheets

OTHER PUBLICATIONS

Glover et al., "Reconstruction of Ultrasound Propagation Speed Distributions in Soft Tissue: Time-of-Flight Tomography", IEEE Transactions on Sonics and Ultrasonics, vol. SU-24, No. 4, Jul. 1977, pp. 229-234.

Lavallee, L. et al., "Matching of Medical Images for Computed and Robot Assisted Surgery", Annual International Conference of the IEEE Engineering in Medicine and Biology Society, vol. 13, No. 1, 1991, pp. 39-40.

Shipley, J.A., et al., "Automated Quantitative Volumetric Breast Ultrasound Data-Acquisition System", Ultrasound in Med. & Bio., vol. 13, No. 7, Jul. 2005, pp. 905-917.

* cited by examiner

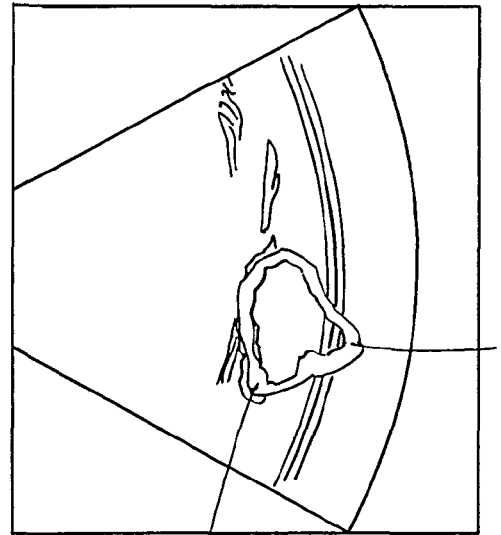
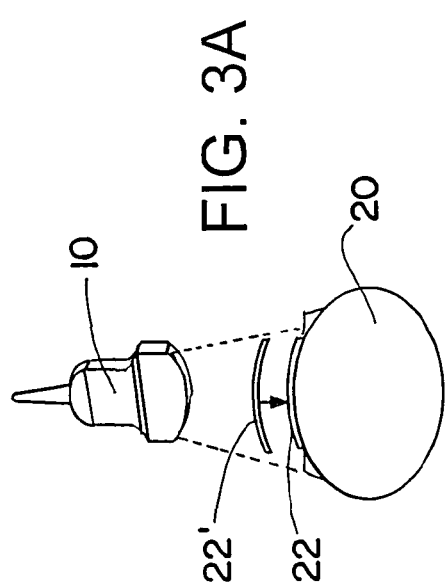
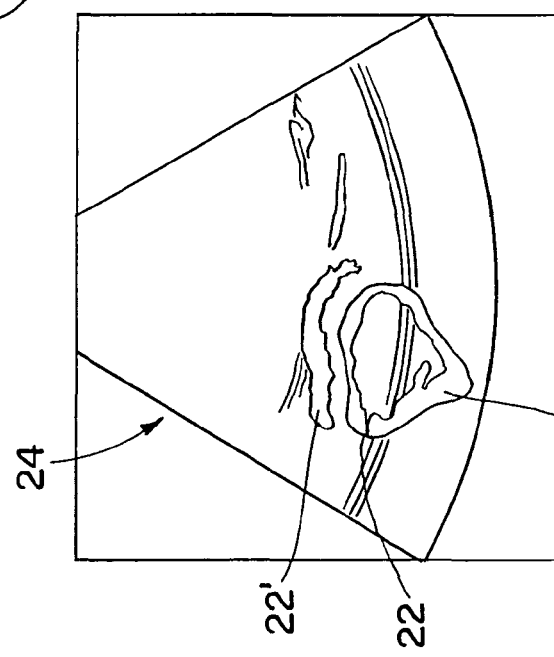

DETERMINING SPEED-OF-SOUND FACTORS IN ULTRASOUND IMAGES OF A BODY

RELATED APPLICATION DATA

This application claims priority of U.S. Provisional Application No. 60/738,548 filed on Nov. 21, 2005, which is incorporated herein by reference in its entirety.

FIELD OF THE INVENTION

The invention relates to determining speed-of-sound factor that affect ultrasound images of a body, and to correcting for such speed-of-sound factors.

BACKGROUND OF THE INVENTION

The fact that the speed of sound is dependent on the medium through which the sound is passing can lead to quantitative inaccuracies in ultrasound image capture (e.g., in image capture for the human body). While structures reproduced in an ultrasound image may be displaced correctly in terms of their shape, an actual distance of actual distances from an ultrasound head to the structures themselves may not be correctly shown in the reproduced ultrasound image.

Correcting for speed-of-sound factors (the effect of different speeds of sound in different penetrated media) is less important in the field of medical diagnostics, as the exact or absolute position of an object relative to the ultrasound head is not of great importance. As a result, only a few attempts have been made to determine or correct speed-of-sound factors or to correct geometric distortions and aberration errors caused by speed-of-sound factors.

An attempt to directly register ultrasound images, wherein only the ultrasound images themselves are used (e.g., two sound images in which corresponding structures are sought) is know from an article by Kruücker et al. entitled "Sound Speed Estimation Using Automatic Ultrasound Registration", from IEEE Transaction on Ultrasonic Ferroelectrics and Frequency Control, 51(9): 1095 to 1106, 2004. These attempts, however, suffer greatly from significant distortions in the captured image data, from a large number of artefacts, problems with collecting data due to scattering effects, and numerical difficulties.

Another approach for taking into account or correcting different speed-of-sound factors, proposed in Barratt et al. "Self-Calibrating Ultrasound-to-CT Bone Registration" from MICCAI (Conference Proceedings), LNCS 3749, Springer Publishing, pages 605 to 612, is to additionally optimize scaling parameters during three-dimensional registration of ultrasound data sets, for example onto a CT data set. In this method the parameters relevant to the essential recording geometry of the ultrasound imaging process may be integrated into the registration method. Since in this method, optimization treats all ultrasound tomographs equally, the scaling parameters are adapted overall. Thus, the speed-of-sound factors only can be estimated or corrected overall.

Speed-of-sound factors may be locally estimated to some extent in methods for time-of-flight ultrasound tomography. This has been performed, for example, in Glover, Sharp: "Reconstruction of Ultrasound Propagation Speed Distributions in Soft Tissue: Time-of-Flight Tomography" from IEEE Transactions on Sonics and Ultrasonics, Volume 24, No. 4, pages 299 to 234, 1977. However, due to technical limitations, such as, for example, noise, geometric distortions, low sound penetration and other artefacts, as well as inherent mathematical properties, in particular the numerical instability of the mathematics to be solved for reconstructing the speed-of-sound factors, these approaches are associated with significant difficulties that severely restrict the practical use of the methods for diagnostic purposes as well as for assisting medical navigation methods. The data ascertained in this manner are not reliable for precisely estimating speed-of-sound factors.

SUMMARY OF THE INVENTION

The present invention provides a system and method that enables speed-of-sound factors in ultrasound images of a body to be determined. The method can include:
  capturing at least two ultrasound images of an internal body region from different directions;
  registering the ultrasound images or specific sets of ultrasound images, two-dimensionally or three-dimensionally, with respect to a corresponding region in a body reference model;
  comparing the two-dimensional registration of each ultrasound image with the registration of at least one other ultrasound image captured from a different direction, or with another reference registration; and
  determining the speed-of-sound factor for each individual ultrasound direction from the comparison of reference model point distances for a particular registered structure.

The speed-of-sound factors can be robustly and reliably determined or also corrected, because a reliable reference, such as the reference model, can be used. This reference model can be registered in a spatial coordinate system beforehand using a known medical tracking and/or navigation system. The reference model therefore represents a reliable reference and that can be used to implement a method of comparison for the ultrasound images. As used herein, the term "registration" refers to an assignment of structures of points on structures in different image data sets, e.g. essentially identifying identical points, lines or regions in different image data sets or images. Ultrasound images need not be registered onto each other, which is advantageous when one considers that the images comprise numerous distortions, and only provide partial information (dependent on direction) on anatomical structures.

Individual ultrasound tomographs or groups of the same can be individually registered (as opposed to overall registration, such as is proposed in the article by Barratt et al. described above). It is possible to estimate the speed-of-sound or speed-of-sound factors for each line of sight from a combination of these individual registrations or a comparison with a reference registration. It is thus possible to correct the speed-of-sound comprehensibly, in more detail and robustly. It is possible to develop specific strategies for acquiring the ultrasound data in order to optimize the estimation of the speed-of-sound in relevant regions. In principle, a (partial) ultrasound tomography (time-of-flight tomography) also may be performed using this approach, wherein reference may be made to the reference model so as to ensure that the speed-of-sound are reliably estimated.

The body reference model can comprise an image data set from a medical imaging method, in particular a CT image data set, an MR image data set, a SPECT of PET image data set or an x-ray projection data set. The body reference model also can comprise an image data set that includes a statistical or geometric model of a body.

The various ultrasound capturing means can lie substantially within one plane, and preferably exhibit an angle of substantially 20 degrees to 30 degrees to each other. It is possible to configure the method such that the ultrasound and model image data sets are roughly or preliminarily registered in three-dimensions, before they are actually registered in tow or three dimensions. Depending on the embodiment, the region of the reference model to be registered can be a two-dimensional region, an ultrasound tomograph or a three-dimensional spatial region.

Two-dimensional registration of each ultrasound image can be compared with the registration of just one, a few or all of the other ultrasound images, wherein the images from a different direction may be captured in substantially the same plane.

The point distances for a number of ultrasound images or sets of ultrasound images from different directions can be compared simultaneously. It is possible to compare the point distances for the ultrasound images or sets of ultrasound images by calculating intersection points of two ultrasound lines of view from different directions that identify the same point in the reference model. It is also possible to determine the speed-of-sound factors iteratively, using a medial three-dimensional registration method, for example.

The invention further provides a correcting method for the speed-of-sound factors in ultrasound images, wherein the speed-of-sound factors can be determined in accordance with one of the methods described herein, and wherein compensations may be made to the speed-of-sound factors. Compensating can include eliminating or reducing local differences in the speed-of-sound or speed-of-sound factor. Compensating also can include integrating a relaxation criterion into the calculation of the speed-of-sound factors.

The invention further relates to a program which, when it is running on a computer or is loaded onto a computer, causes the computer to perform a method as described above. It also relates to a computer program storage medium comprising such a program.

BRIEF DESCRIPTION OF THE DRAWINGS

The forgoing and other features of the invention are hereinafter discussed with reference to the drawings.

FIGS. 3A-3C are schematic representations of an exemplary registration of a body structure with the aid of a reference model and on the basis of ultrasound images in accordance with the invention

DETAILED DESCRIPTION

Figure 1:
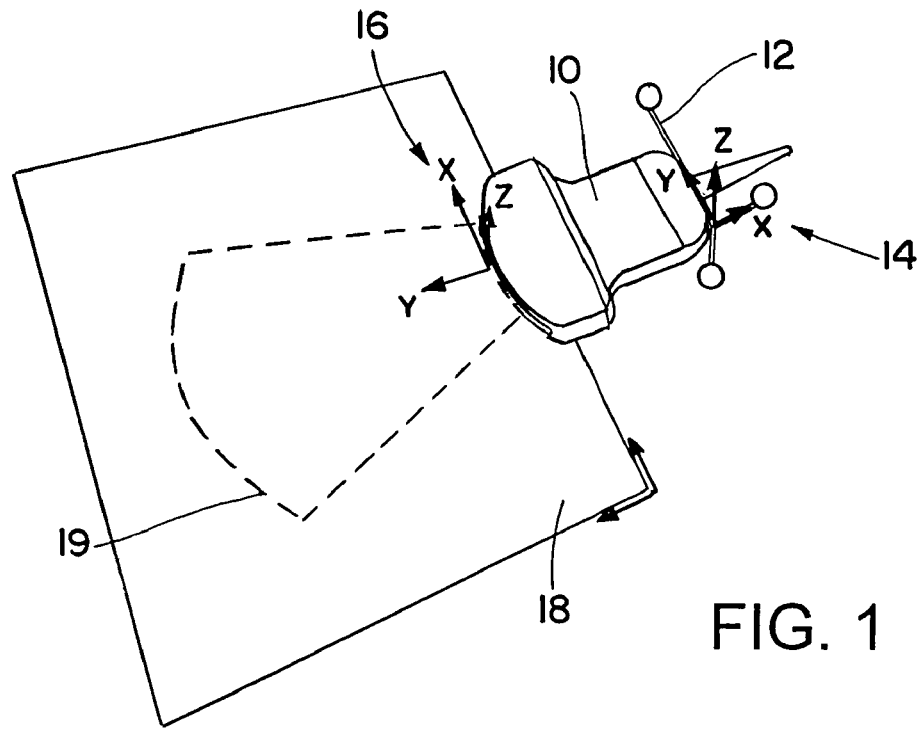
FIG. 1 illustrates an exemplary ultrasound head scanning an image region at least part of which is on an image plane in accordance with the invention.

FIG. 1 shows an exemplary ultrasound head 10 that may be used in conjunction with the present invention. With the aid of a reference star 12, which is shown attached to the head 10 in FIG. 1, the head 10 can be positionally localized and tracked with the aid of a medical tracking an/or navigation system. Said navigation system (not shown) may use a first coordinate system x,y,z, indicated by the reference sign 14.

The head 10 can capture images in a plane 18 within the ultrasound image window 19 (also referred to below as an ultrasound tomograph). The ultrasound tomograph 19 can lie in the plan 18, and the head essentially can span its own coordinate system, which is likewise referred to as x,y,z and is indicated by the reference sign 16. If the reference star 12 is fixed, the coordinate systems 14 and 16 essentially do not differ.

Figure 2:
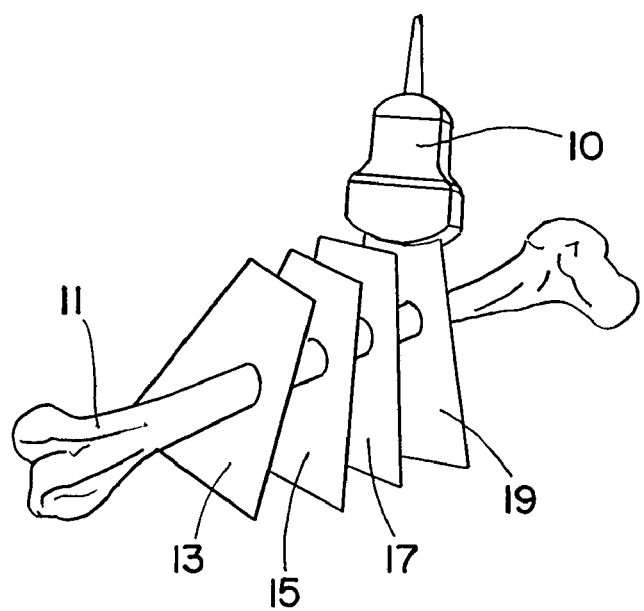
FIG. 2 illustrates various image regions of an exemplary ultrasound head in different planes on a bone in accordance with the invention.

FIG. 2 essentially shows the head 10 acquiring ultrasound data (e.g., ultrasound images of a bone 11, which are captured by tomographs 13, 15, 17 and 19). the tomographs 13, 15, 17 and 19 lie in different planes and are at an angle with respect to each other. In the ultrasound images, a structure (for example, a mid section of the bone 11) can then be mapped as a curved line, and this is schematically shown in FIG. 3A. In very general terms, using the head 10 an ultrasound recording is taken of the structure 20. The structure 20 includes an upper edge 22, which can be shown in the ultrasound image.

FIG. 3A can be envisioned such that the structure 20 reproduces an actual position, for example, as may be determined from an image data set registered in the operating theater (e.g. a CT data set) or as localized or registered by means of a navigation system in the operating theater. However, due to speed-of-sound factors, the ultrasound head 10 does not perceive or otherwise detect the edge 22 of the structure 20 at its actual position, but rather at a different position, namely at the shifted or skewed position 22'.

This scenario is shown in FIG. 3B, in which an ultrasound recording (e.g., a tomographic 24) is shown. In the tomograph 24, the structure 20 is superimposed on its actual position (e.g., with the upper edge 22 at the actual spatial position). The white edge 22' shows where the ultrasound head 10 perceives the edge 22 to be. As can be seen, there is a position error between the actual position and the perceived position. This difference between the actual and perceived positions in the superimposed image data sets provides a quantitative statement of the effect the speed-of-sound factors have on the determination of position, distance and/or length in the ultrasound image. Using this data (i.e., the knowledge of the effect of the speed-of-sound factors), it is then possible to compensate for these differences in the actual and perceived position, distance and/or length of the edge 22. Once compensated, the ultrasound head 10 can map the edge 22' of the structure exactly where the actual edge 22 of the reference model data set is mapped, as shown in FIG. 3C. The compensation made to the speed-of-sound factors then can determined for at least one direction of view. As a result, ultrasound images that are quantitatively meaningful can hence be produced.

Figure 4:
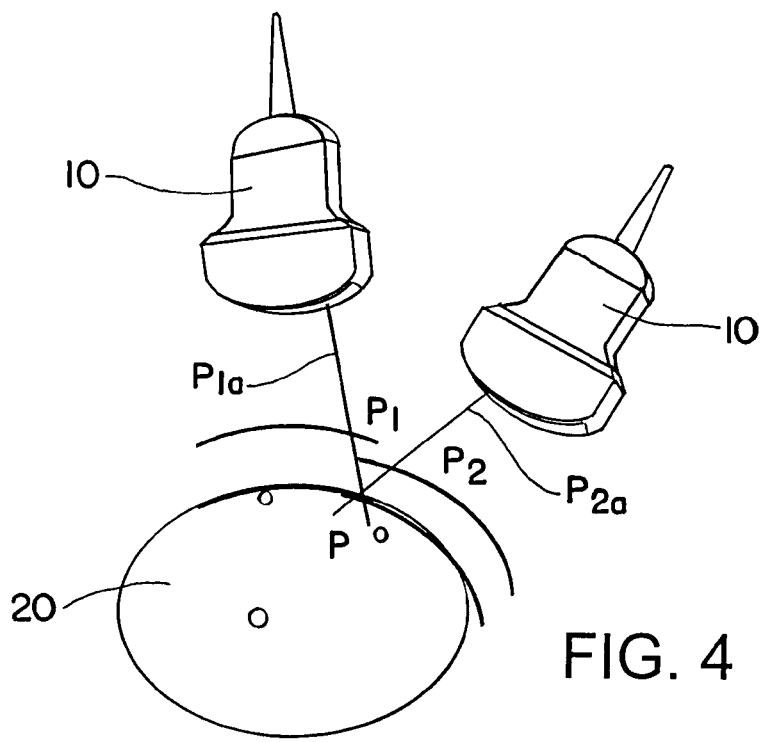
FIG. 4 shows a comparison of different registrations using point references in accordance with the invention.

FIG. 4 shows a comparison of different registrations with the aid of point references in ultrasound tomographs recorded in approximately the same plane, but angularly offset. The ultrasound images can be two-dimensionally registered in a plane spanned in this manner, wherein the distance can be captured, as described above, point by point, FIG. 4 shows how registration may be performed using the point "p" on the structure 20. Since the speed-of-sound factors act in the "direction of view" of the ultrasound head, it is difficult to precisely capture the point "p" from just one direction (e.g., it is difficult to determine a distance from the head 10 to the point "p"). However, the distance of the point "p" from the head 10 can be ascertained via multiple mappings (e.g., mappings "$p_1$" and "$p_2$"). Because the two ultrasound tomographs comprising the mappings "$p_1$" and "$p_2$" are offset from one another by the predetermined angle, a guidance error can be corrected, a location can be correctly captured. Using this information, it is possible to introduce an equally exact compensation to the image data.

For example, the first mapping "$p_1$" and the second mapping "$p_2$" of the point "p" can be generated, wherein "$p_1$" and "$p_2$" are in the same plane but offset from one another by a predetermined angle (e.g., 20 to 30 degrees). It is known that the point "p" lies somewhere along the "direction of view" for each mapping (e.g, along the lines $p_{1a}$ and $p_{2a}$). By determining the intersection of the lines $p_{1a}$ and $p_{2a}$ (e.g., via triangulation), the location of the point "p" relative to the head 10 can be ascertained. Then, the perceived location of the point "p" and the ascertained location of the point "p" can be compared to determine the speed-of-sound factors for that particular direction of view, and these factors can be taken into account to correct the ultrasonic image.

Figure 5:
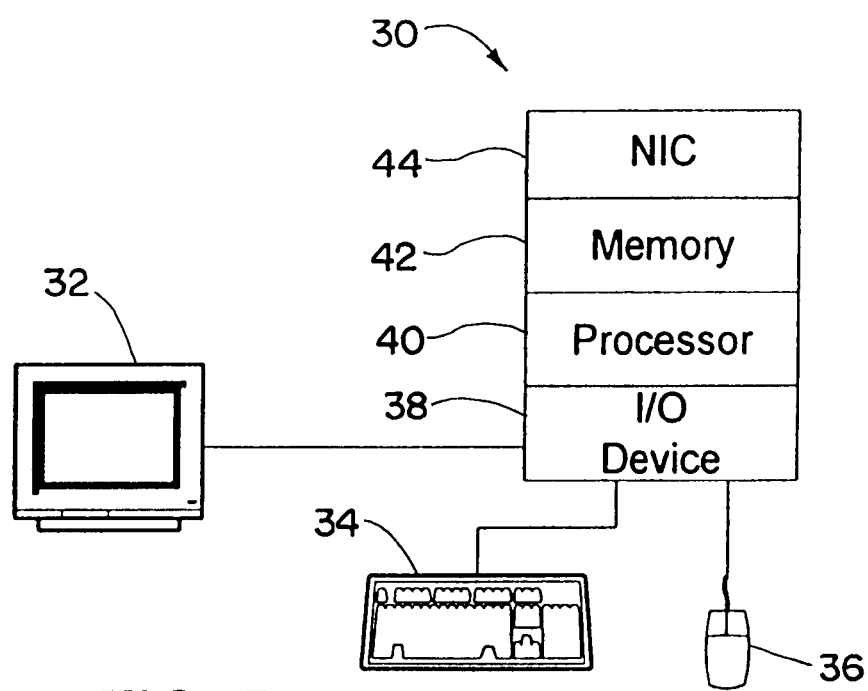
FIG. 5 is a block diagram of an exemplary computer system that can be used to carry out the method in accordance with invention.

FIG. 5 illustrates a computer system 30 that may be used to implement the method described herein. The computer system 30 may include a display 32 for viewing system information, and a keyboard 34 and pointing device 36 for data entry, screen navigation, etc. A computer mouse or other device that points to or otherwise indentifies a location, action, etc. e.g., by a point and click method or some other method, are examples of a pointing device 36. Alternatively, a touch screen (not shown) may be used in place of the keyboard 34 and pointing device 36. The display 32, keyboard 34 and mouse 36 communicate with a processor via an input/output device 38, such as a video card and/or serial port (e.g., a USB port or the like).

A processor 40, such as an AMD Athlon 64® processor or an Intel Pentium IV® processor, combined with a memory 42 execute programs to perform various functions, such as data entry, numerical calculations, screen display, system setup, etc. The memory 42 may comprise several devices, including volatile and non-volatile memory components. Accordingly, the memory 42 may include, for example, random access memory (RAM), read-only memory (ROM), hard disks, floppy disks, optical disks (e.g., CDs and DVDs), tapes, flash devices and/or other memory components, plus associated drives, players and/or readers for the memory devices. The processor 40 and the memory 42 are coupled using a local interface (not shown). The local interface may be, for example, a data bus with accompanying control bus, a network, or other subsystem.

The memory may from part of a storage medium for storing information, such as application data, screen information, programs, etc. part of which may be in the form of a database. the storage medium may be a hard drive, for example, or any other storage means that can retain data, including other magnetic and/or optical storage devices. A network interface card (NIC) 44 allows the computer system 30 to communicate with other devices.

A person having ordinary skill in the art of computer programming and applications of programming for computer systems would be able in view of the description provided herein to program a computer system 30 to operate and to carry out the functions described herein. Accordingly, details as to the specific programming code have been omitted for the sake of brevity. Also, while software in the memory 42 or in some other memory of the computer and/or server may be sued to allow the system to carry out the functions and features described herein the accordance with the preferred embodiment of the invention, such functions and features also could be carried out via dedicated hardware, firmware, software, or combinations thereof, without departing from the scope of the invention.

Computer program elements of the invention may be embodied in hardware and/or in software (including firmware, resident software, micro-code, etc.). The invention may take the form of a computer program product, which can be embodied by a computer-usable or computer-readable storage medium having computer-usable or computer-readable program instructions, "code" or a "computer program" embodied in the medium for use by or in connection with the instruction execution system. In the context of this document, a computer-usable or computer-readable medium may be any medium that can contain, store, communicate, propagate, or transport the program for use by or in connection with the instruction execution system, apparatus, or device. The computer-usable or computer-readable medium may be, for example but not limited to, an electronic, magnetic, optical, electromagnetic, infrared, or semiconductor system, apparatus, device, or propagation medium such as the Internet. Note that the computer-usable or computer-readable medium could even be paper or another suitable medium upon which the program is printed, as the program can be electronically captured, via, for instance, optical scanning of the paper or other medium, then compiled, interpreted, or otherwise processed in a suitable manner. The computer program product and any software and hardware described herein form the various means for carrying out the functions of the invention in the example embodiments.

Although the invention has been shown and described with respect to a certain preferred embodiment or embodiments, it is obvious that equivalent alterations and modifications will occur to others skilled in the art upon the reading and understanding of this specification and the annexed drawings. In particular regard to the various functions performed by the above described elements (components, assemblies, devices, compositions, etc.), the terms (including a reference to a "means") used to described such elements are intended to correspond, unless otherwise indicated, to any element which performs the specified function of the described element (i.e., that is functionally equivalent), even though not structurally equivalent to the disclosed structure which performs the function in the herein illustrated exemplary embodiment or embodiments of the invention. In addition, while a particular feature of the invention may have been described above with respect to only one or more of several illustrated embodiments, such feature may be combined with one or more other features of the other embodiments, as may be desired and advantageous for any given or particular application.

What is claimed is:

1. A method for determining speed-of-sound factors in ultrasound images of a body, comprising:
    capturing at least two ultrasound images of an internal body region from different directions;
    registering the at least two ultrasound images with respect to a corresponding region of a body reference model;
    comparing, using a processor, body reference model point distances for a particular registered structure in the registrations of the at least two ultrasound images to each other; and
    determining the speed-of-sound factor for each individual ultrasound direction in the body region from the comparison of body reference model point distances.

2. The method according to claim 1, wherein registering includes using a body reference model that includes an image data set from a medical imaging method.

3. The method according to claim 2, wherein using a body reference model includes using an image data set derived from at least one of a CT image data set, an MR image data set, a SPECT or PET image data set, or an x-ray projection image data set.

4. The method according to claim 1, wherein registering includes using a body reference model that includes an image data set comprising a statistical or geometric model of the body.

5. The method according to claim 1, wherein capturing at least two ultrasound images includes capturing at least two ultrasound images that lie substantially within one plane.

6. The method according to claim 5, wherein capturing at least two ultrasound images that lie substantially within one plane includes capturing at least two ultrasound images that exhibit an angle of substantially 20 degrees to 30 degrees with respect to each other.

7. The method of claim 1, wherein registering includes registering the at least two ultrasound images two-dimensionally or three-dimensionally.

8. The method according to claim 7, wherein registering includes preliminarily registering the ultrasound images and reference model in three dimensions before they are two-dimensionally or three-dimensionally registered.

9. The method according to claim 7, wherein comparing includes comparing the two-dimensional registration of each ultrasound image with the registration of at least one of the other ultrasound images, wherein the images from a different direction are captured in substantially the same plane.

10. The method according to claim 1, wherein registering includes registering a region of the reference model that comprises a two-dimensional region, an ultrasound tomograph or a three-dimensional spatial region.

11. The method according to claim 1, wherein comparing includes simultaneously comparing registrations for a plurality of ultrasound images or sets of ultrasound images from different directions.

12. The method according to claim 1, wherein comparing includes comparing the point distances for the ultrasound images or sets of ultrasound images by calculating intersection points of two ultrasound lines of view from different directions that identify the same point in the reference model.

13. The method according to claim 1, further comprising using a medical three-dimensional registration method to determine the speed-of-sound factors iteratively.

14. The method according to claim 1, further comprising compensating for the speed-of-sound factors once they are determined.

15. The method according to claim 14, wherein compensating includes eliminating or reducing local differences in the speed-of-sound or speed-of-sound factors.

16. The method according to claim 14, wherein compensating includes integrating a relaxation criterion into calculating the speed-of-sound factors.

17. A non-transitory computer readable medium with an executable program stored thereon for determining speed-of-sound factors in ultrasound images of a body, wherein the program instructs a processor to perform the following steps:
   direct the capture of at least two ultrasound images of an internal body region from different directions;
   register the at least two ultrasound images with respect to a corresponding region of a body reference model;
   compare body reference model point distances for a particular registered structure in the registrations of the at least two ultrasound images to each other; and
   determine the speed-of-sound factor for each individual ultrasound direction in the body region from the comparison of body reference model point distances.

* * * * *